United States Patent
Sim

(12) 
(10) Patent No.: US 6,365,162 B1
(45) Date of Patent: Apr. 2, 2002

(54) BODY COSMETIC PIGMENT COMPOSITION AND ITS PRODUCTION METHOD

(75) Inventor: Ho Chin Sim, Kyounggi-Do (KR)

(73) Assignee: DA MIN Enterprises Ltd., Seoul (KR)

( * ) Notice: Subject to any disclaimer, the term of this patent is extended or adjusted under 35 U.S.C. 154(b) by 0 days.

(21) Appl. No.: 09/483,484

(22) Filed: Jan. 14, 2000

Related U.S. Application Data

(63) Continuation-in-part of application No. 09/151,984, filed on Sep. 11, 1998, now abandoned.

(30) Foreign Application Priority Data

Dec. 3, 1997 (KR) ............................................ 97-47853

(51) Int. Cl.⁷ .............................................. A61K 35/78
(52) U.S. Cl. .................................................. 424/195.17
(58) Field of Search ..................................... 424/195.17

(56) References Cited

U.S. PATENT DOCUMENTS

| | | | |
|---|---|---|---|
| 4,393,045 A | * | 7/1983 | Henderson et al. ............ 424/95 |
| 4,446,051 A | * | 5/1984 | Berthod et al. .............. 252/309 |
| 4,943,432 A | | 7/1990 | Beiner ........................ 424/647 |
| 5,547,997 A | | 8/1996 | Kludas ........................ 514/195 |

FOREIGN PATENT DOCUMENTS

| | | |
|---|---|---|
| CH | 686 999 | 8/1996 |
| FR | 2 659 551 | 9/1991 |
| JP | 5-953 | 1/1993 |
| JP | 5-177158 | 5/1993 |
| JP | 10-194732 | 7/1998 |

OTHER PUBLICATIONS

Abdek–Fattah et al., "Selective isolation of glycoprotein materials from the green seaweed Ulva lactuca", Pakistan Journal of Biochemistry, 1987, vol.20, No. 1–2, pp. 61–65.
Ayed et al., Recovery of ammonium added to soils and clay minerals: Acta Agriculture Scandinavica, 1975, 25, 237–241.
Koyama et al., Investigating the nutritional medicinal, and cosmetic values of seaweeds and their extracts:, Erds Int., 1983 1(2), 85–117.

* cited by examiner

*Primary Examiner*—Sandra E. Saucier
*Assistant Examiner*—Vera Afremova
(74) *Attorney, Agent, or Firm*—William A. Simons; Wiggin & Dana

(57) ABSTRACT

The present invention is related to a body cosmetic composition used for enhancing elasticity of the skin and losing a weight, and its producing method, in which the body cosmetic composition includes the marine plant's extract including various ingredients such as calcium, potassium, iodine, selenium, alginic acid, and the like, extracted from brown seaweed, sea tangles or combinations thereof, the loess's extract including silica, aluminum, magnesium and various minerals obtained from the loess, and the shell's extract extracted from oyster shells, mussel shells, bivalve shells and combinations thereof. The cosmetic composition provides elasticity in excessively sagged muscles, has an effect on losing weight, contributes to prevent the skin from aging by providing the inorganic substance, the mineral and the like for skin cells through the capillary vessel connected to the skin, and further give effects to maintain physical fitness.

4 Claims, 3 Drawing Sheets

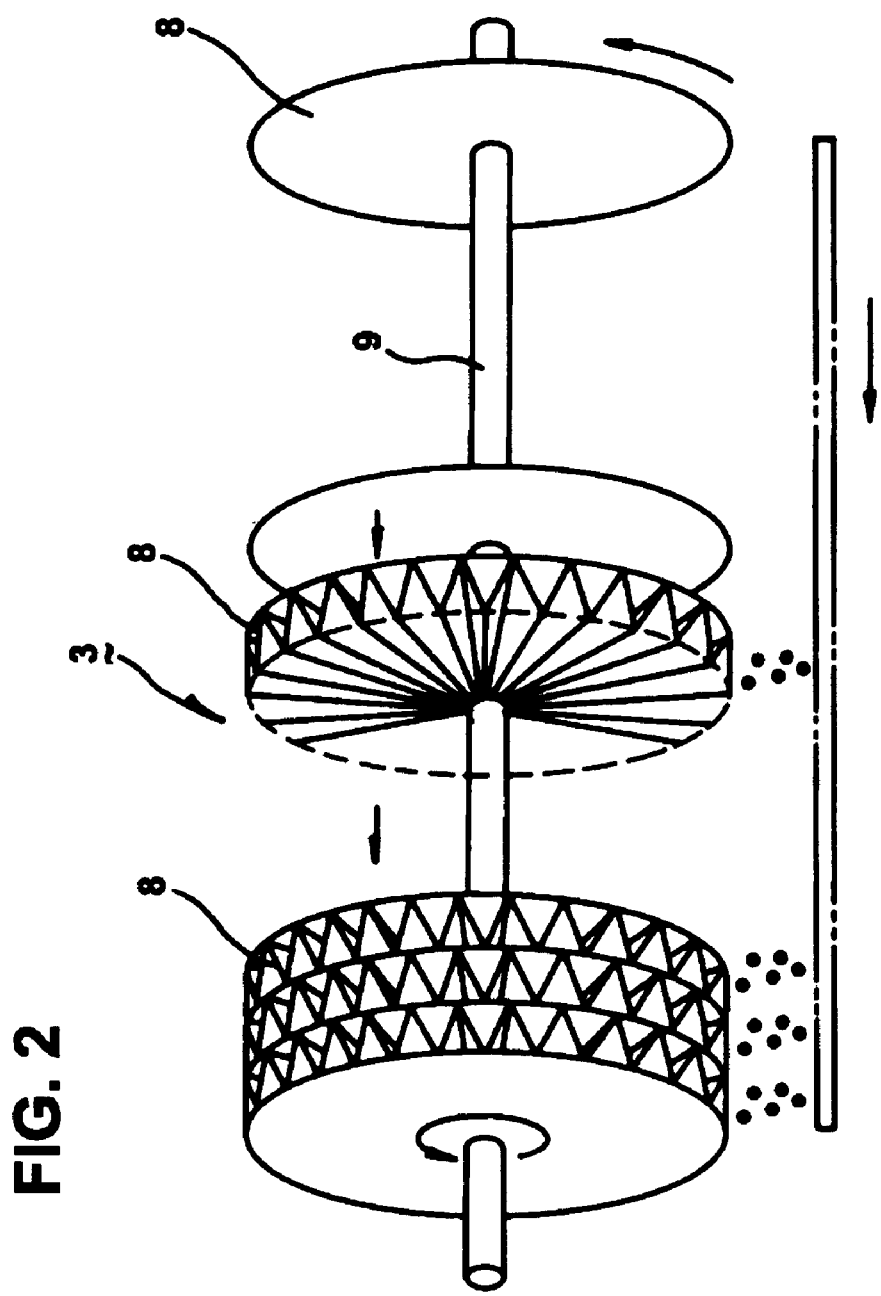

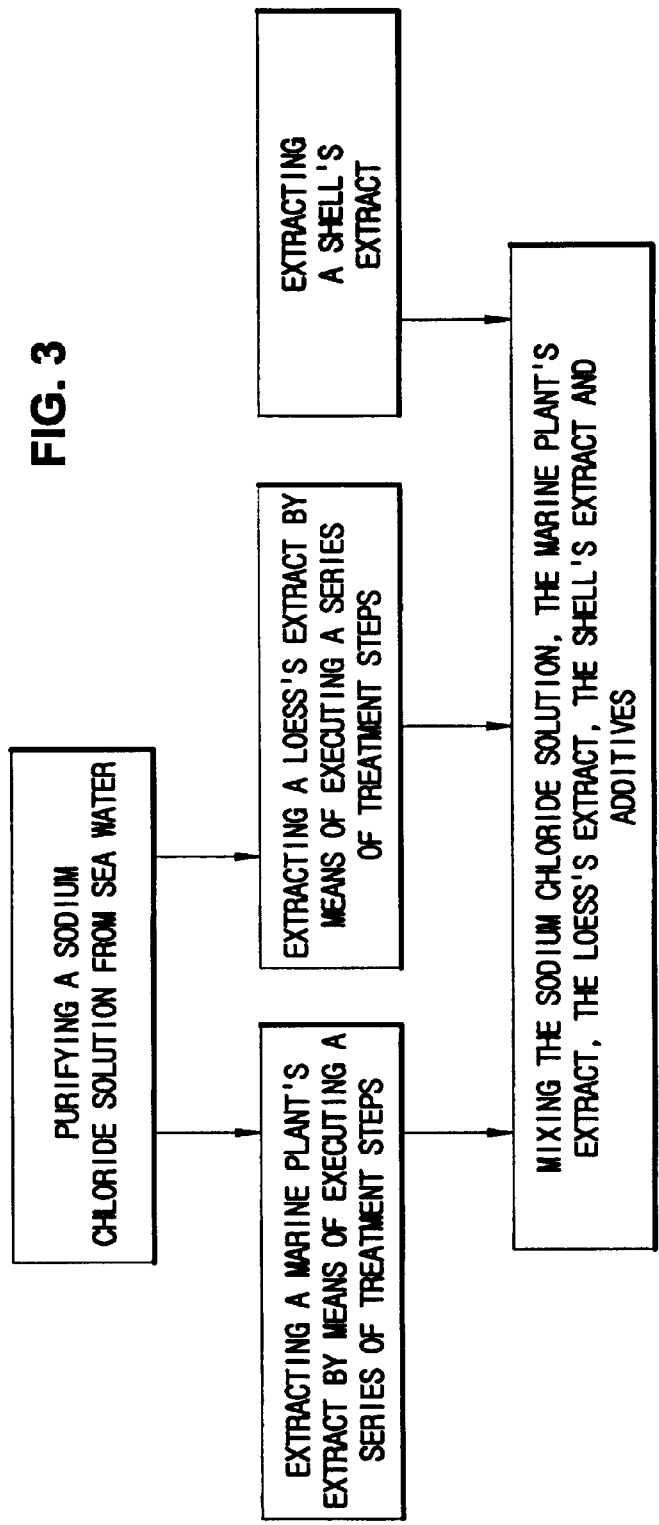

BODY COSMETIC PIGMENT COMPOSITION AND ITS PRODUCTION METHOD

CROSS REFERENCE TO RELATED APPLICATION

This application is a continuation-in-part of U.S. patent application Ser. No. 09/151,984 entitled "BODY COSMETIC PIGMENT COMPOSITION AND ITS PRODUCTION METHOD" filed on Sep. 11, 1998, now abn. That parent application is incorporated herein by reference in its entirety.

BACKGROUND OF THE INVENTION

The present invention is related to a body cosmetic composition and its producing method, and particularly, to a body cosmetic composition for enhancing skin elasticity of body and losing weight.

As civilization progresses, people ingest more meats than vegetables because of living conditions being abundant, and are apt to be lacking in exercise owing to convenient traffic, so increasing the number of obese people. But obesity is a major cause of various diseases. Particularly, flesh of belly and waist is an index of health and is taken seriously in beauty. For the foregoing reasons, there is a need for a body cosmetic composition that enhances skin elasticity and help losing weight.

SUMMARY OF THE INVENTION

The present invention is directed to a body cosmetic composition and its producing method that satisfies the above needs.

An object of the present invention is to provide a body cosmetic composition includes marine plant's extract including various ingredients, sodium chloride solution purified from sea water, loess's extract including various inorganic ingredients, shell's extract and additives, in more particular, to provide the body cosmetic composition comprising 20–40 parts by weight of marine plant's extract, 10–30 parts by weight of loess's extract, and 5–10 parts by weight of shell's extract per 100 weight part of sodium chloride solution.

Preferably, the marine plants are selected from brown seaweed, sea tangle and/or combination thereof, and the marine plant's extract includes calcium, potassium, iodine, selenium, alginic acids and various organic ingredients. The loess is preferably selected from Kaolinite, Montmorlillonite and/or combinations thereof and the loess's extract includes silica, aluminum, magnesium, and various minerals. Also, preferably the shells are selected from oyster, clam, mussel, bivalve and/or combination thereof, and the shell's extract includes various ingredients such as $CaCO_3$, $K_2O$, $P_2O_5$, N, Mg, Mn, Fe, Zn, B and so on.

Another object of the present invention is to provide a method for producing a body cosmetic composition as shown in FIG. 3. The method for producing the body cosmetic composition comprises the steps of: purifying sodium chloride solution from sea water; extracting marine plant's extract from marine plants by means of executing a series of treatment steps; extracting loess's extract from loess by means of executing a series of treatment steps; extracting shell's extract, and mixing the sodium chloride solution, the marine plant's extract, the loess's extract and the shell's extract with additives uniformly.

The step of purifying sodium chloride solution from seawater comprises preferably steps of drawing the sea water in a tank on the ground; fitting the concentration thereof to be 2.0–2.2 weight % by measuring concentration with use of a salinity concentration measurer; purifying sodium chloride solution by eliminating impurities in the sea water, with a purifier as shown in FIG. 1 and FIG. 2.

Preferably, the step of extracting marine plant's extract comprises steps of deodorizing the marine plant's odor; breaking down tissues of the marine plant by means of freeze thaw cycles repeatedly; pulverizing a mixture which the broken tissues are added to the sodium chloride solution with use of a pulverizer; filtrating the pulverized mixture; and treating the filtrated mixture with organic acid to adjust pH which is suitable for applying to the skin, in particular, the freeze thaw cycle are carried out 1–5 times repeatedly which consists of freezing the marine plants in a freezer at a temperature from $-7°$ C. to $-3°$ C. for 48 hours and thawing the frozen marine plants in a thawing device at a temperature from $1°$ C. to $-5°$ C. for 6 hours.

The step of extracting loess's extract, preferably, comprises steps of separating minute loess by means of pulverizing loess and screening the pulverized loess; extracting a viscous materials including silica, Al, Mg, and various minerals by means of taking the sunk portion of the loess solution which is kept in the dark place for 1 hour after dissolving the minute loess in the purified water, and then agitating the mixture, and then filtrating the mixture; mixing the viscous materials with the sodium chloride solution to form a viscous material solution; filtrating after agitating the viscous material solution for 3–4 hours; adding NaOH to the filtrated solution by pH7.0; and purifying the solution added NaOH when sudden agglutination is observed to form the loess's extract.

Also, the step of extracting shell's extract, preferably, comprises steps of pulverizing shells: mixing the pulverized shells and water at the ratio of 1:1; heating the mixture for 30 minutes; and filtrating the heated mixture to extract the shell's extract.

BRIEF DESCRIPTION OF THE DRAWINGS

FIG. 2 is a schematic enlarged perspective view showing a turning circular filtering unit of the sodium chloride solution extracting facility in FIG. 1; and FIG. 3 schematically shows steps of a method for producing the body cosmetic composition of the present invention.

DETAILED DESCRIPTION OF THE INVENTION

Figure 1:
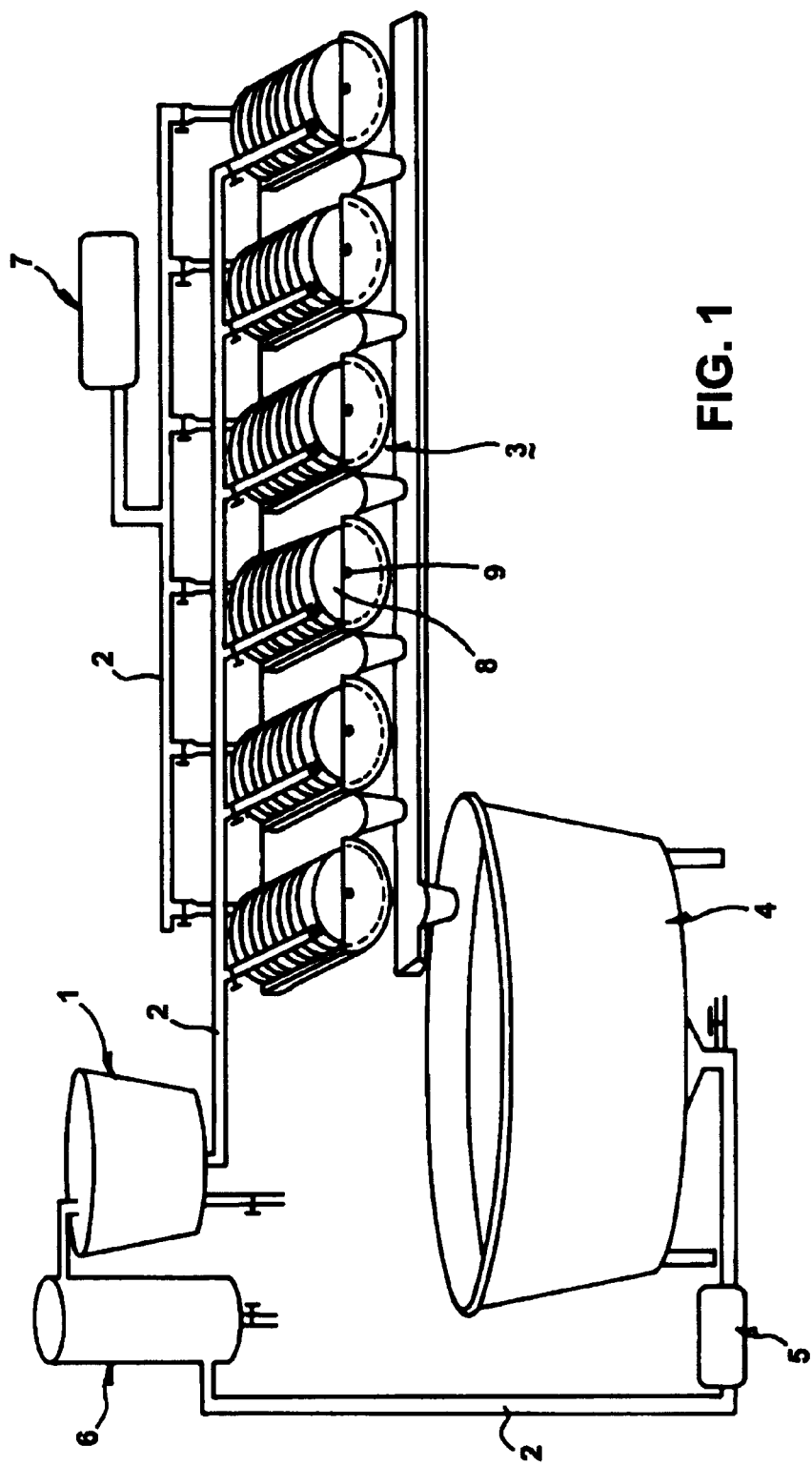
FIG. 1 schematically shows a facility for extracting sodium chloride solution, used for producing the body cosmetic composition of the present invention.

A body cosmetic composition of the present invention comprises the sodium chloride solution, the marine plant's extract which is extracted from marine plants such as brown seaweed, sea tangle, or combination thereof, the loess's extract including silica, aluminum, magnesium, and various minerals, the shell's extract and additives which include fragrance, preservative, colorant and useful material for skin health.

At first, it is explained on roles of the sodium chloride and its purification below.

It is well known that the human body mainly consists of water. The water solves several kinds of nutritive elements and minerals, which are physiological activating materials, and intermediates physiological reactions in cells.

A total amount of water in human body is about 60–70% of body weight, and men generally have higher percentage of water than women, and the fat than the thin. Water in human body is referred to humor, which is divided in two classifications of intracellular humor and extracellular humor.

The intracellular humor is water existing in cells, and is occupying $\frac{2}{3}$ of the humor. The remaining $\frac{1}{3}$ of the humor is dispersed among the extracellular humors. Therefore, in case of an adult of 70 kg in weight, a total amount of the humor is about 40L, in which about 25L corresponds to the intracellular humor and about 15L to the extracellular humor. On the other hand, the extracellular humor is divided into the blood plasma and intercellular humor, which has 1:3 ratio.

Water, which people ingest day after day, is mainly entered through oral system by drinking water or eating foodstuffs containing water. Additionally, it may be generated in the body as a product of the metabolism reaction, although it is a small amount. Usually, about 2,500 ml of water enters into the human body in a day, while about 2,200 ml which is 90% thereof is ingested through the oral system. On the other hand, even if amount of water, lost out of human body, changes according to circumferential temperature or movement degree, in a normal condition, about 900 ml of ingested water is dispersed in the body and excreted by vaporization of respiratory organ and skin, in which human cannot feel sensually the loss of water.

The osmotic pressure means the number of particles solved in a solution per unit volume. While the osmotic pressure of the humor can be controlled by varying the number of the particles or amount of water, a living body controls the osmotic pressure of the humor by varying the amount of water in the body. Such controlling action is achieved by a thirst or an anti-urination hormone.

Because water moves by free diffusion between cells, the extracellular humor and the intracellular humor consequently have equal osmotic pressures. If the osmotic pressure of any humor changes, water is redistributed until the osmotic pressures of both humors become equal.

A major factor for determining the effective osmotic pressure is a concentration of the sodium chloride, which consists 90% of total extracellular solute which causes the effective osmotic pressure. Therefore, the increase and decrease of the concentration of the sodium chloride accompany the change of the osmotic pressure and the cell volume.

When a person ingests water excessively more than that to be excreted, the body is in an excessive state of water. The excessive water then becomes the extracellular humor so to increase the volume of the cells and dilute the solute. Therefore, molecules of water continue moving from the extracellular humor to the intracellular humor until the osmotic pressures of both humors become equal to each other. As a result, more water is distributed in the cells rather than out of the cells, which is a water redistribution phenomenon by volume change of total humor in body.

In addition, when a person ingests a sodium chloride solution at rich concentration, the concentration of the sodium chloride in the extracellular humor is increased. At this time, although much sodium chloride enters into the cells, an excretion rate of the sodium chloride is also increased such that the increase of salt is mainly restricted to the extracellular humor region. Therefore, while water moves until the osmotic of both humors equal to each other, the water redistribution from the intracellular humor to the extracellular humor is promoted.

Also, between the blood plasma and the intercellular humor, water and electrolyte in the blood plasma are let out of blood vessels in level of a capillary vessel by a colloidal osmotic pressure of blood plasma protein. The egress and ingress of humor are balanced by force for drawing the intracellular humor in the blood vessel inversely by the colloidal osmotic pressure of the blood plasma protein. That is a principle of the osmotic pressure. Water is prevented from excessively flowing in by making normal amount of the sodium chloride remaining in the blood plasma with use of the above principle.

When applying the solution containing the sodium chloride on a sagged skin, the concentration of the intercellular humor increases instantaneously by the sodium chloride entered into the capillary vessel. Then the increased concentration makes the water in cells move out of the cells, resulting in excreting water collected among cells through the kidneys out of body.

According to the present invention, purification of sodium chloride solution from seawater comprises steps of: drawing the sea water in a tank on the ground; fitting the concentration thereof to be 2.0–2.2% weight by measuring concentration with use of a salinity concentration measurer; purifying sodium chloride solution by eliminating impurities in the sea water, with a purifier as shown in FIG. 1 and FIG. 2.

Secondly, characteristics of the brown seaweed and the sea tangles and a method for extracting the marine plant's extract is explained herein.

The brown seaweed and the sea tangle contain calcium and potassium in a rich amount, specially the potassium twice as much as sodium. When ingesting plenty of the potassium, the potassium is excreted in company with the sodium in urine, so that preventing water from being supplied extremely to the interior of the body primarily. As a result, because of eliminating surplus water from the body, flesh of belly less hang down and skin of belly is kept elastically.

Additionally, the seaweed and the sea tangle contain iodine in a rich amount. The iodine is closely related to the thyroid gland, so lack of the iodine may cause the thyroid gland diseases. Specially, it is known that abnormality of hormone secretion leads to gain a weight, while a functional deterioration of the thyroid gland can be prevented by ingesting the brown seaweed and the sea tangles among the kelps.

The brown seaweed and the sea tangles also contain selenium. The selenium is a component of glutathione-peroxidase, which prevents cells from being oxidized or broken down. As a result, because of the selenium preventing cells from oxidized or broken down, selenium gives the skin to elasticity. In addition, the selenium exists in sea water and soil in a very small amount and is a rare mineral essential to a metabolism of the human body.

In particular, the seaweed and the sea tangles contain a lot of alginic acids. According to experiments of injecting alginic acids into laboratory rat, we know the level of neutral lipid and cholesterol decrease. As a result, a lot of alginic acids helps lose a weight by aiding lipids to resolve. Also, the seaweed and the sea tangles contain various antibacterial materials, physiological activator, and various minerals shown in table 1.

[TABLE 1]

Analysis table of ingredients of brown seaweed and sea tangle

|  |  | brown seaweed (live) | sea tangle (live) |
|---|---|---|---|
| Water (%) |  | 88.8 | 91.0 |
| Protein (%) |  | 2.1 | 1.1 |
| Lipid (%) |  | 0.2 | 0.2 |
| Carbohyrate (g) | Saccharide | 4.4 | 3.6 |
|  | Cellulose | 0.6 | 0.6 |
| Lime powder (g) |  | 3.9 | 3.5 |
| Inorganic Matter (mg) | Calcium | 153 | 103 |
|  | Phosphorus | 40 | 23 |
|  | Iron | 1.0 | 2.4 |
|  | Sodium | — | 554 |
|  | Potassium | — | 1,242 |
| Vitamin | A  Vitamin A (R, E) | 308 | 129 |
|  | Retinol (ug) | 0 | 0 |
|  | Betacarotin (ug) | 1,854 | 774 |
|  | B  Thiamine (mg) | 0.06 | 0.03 |
|  | Riboflavin (mg) | 0.16 | 0.13 |
|  | Niacin (mg) | 1.0 | 1.1 |
|  | Ascorbic acid (mg) | 18 | 14 |

In the other hand, when eating the brown seaweed and the sea tangles, they are crushed by teeth, resolved by digestive enzymes, and then absorbed in viscera in ion state. Therefore, it is important for various ingredients of the brown seaweed and the sea tangles to be extracted in the ion state and absorbed in capillaries through skin in a simple manner without the numerous processes, as described above.

To extract the marine plant's extract, which are ions of various ingredients, from the brown seaweed and the sea tangle is important first of all in the present invention. But, heating to about 100° C. for extraction may result in breaking the physiological activator and several minerals.

In the present invention, the extract of the brown seaweed and the sea tangles is extracted by freezing and thawing them repeatedly because it derives tissue destruction of leaf body cells so to easily extract various ingredients.

The leaf body is most easily destroyed when repeatedly freezing to −7° C. and then thawing to +5° C. On the contrary, when repeatedly freezing to −3° C. and thawing to +1° C., the cell tissue destruction is decreased but as acceptable degree. It is understood that the leaf body tissue cell can be destroyed by generating freezing points. Then, the leaf body is pulverized by a pulverizer, such as Polytron pt2000, in 6,000 revolutions per minute for destroying more than 90% of the leaf body. When pulverizing, it is difficult to pulverize the leaf body only. Therefore, for pulverizing the leaf body effectively, sodium chloride solution mixed with the leaf body under consideration of concentration in the leaf body, so the sodium chloride solution is at about 2.0–2.2% concentration. On the other hand, the brown seaweed and the sea tangles, which are live, frozen, stored, or treated, are all available.

Thirdly, an ion exchange for securing viscous materials will be explained. The viscous materials are extracted from loess. The viscous materials show a surprising effect to provide elasticity to the skin. The viscous materials of the loess are difficult to obtain because they are combined in ionic bonds. But, when using sea water, they are easily obtained by method of ion substitution. The viscous materials are secondary minerals fully containing minerals such as silica, aluminum, magnesium and so on.

The loess is generally designated as a part of soil which has yellow color. But the color of the soil varies according to ingredients contained in the soil. The soil is mostly recombined in a generating process, and has various forms according to circumferential condition. The soil is generally classified in five types, such as Kaolinite, Montmorlillonite, Illite, Chlorite, and Vermiculite. The classification follows a component ratio of silica and aluminum.

The experiments of viscous characteristics of the soils show that the Kaolinite and the Montmorlillonite have distinguishable viscous effect. In special, it is shown that the viscous materials provide hard tightness on the skin when applied thereon. The degree of the tightness is Montmorlillonite>Kaolinite>Chlorite>Illite>Vermiculite. Therefore, according to the result of the experiments, it is effective to use the Kaolinite and the Montmorlillonite as a viscous material.

To obtain suitable viscous materials, the natural loess are pulverized finely. They pass through a sieve two or three times so to select minute ones, then completely solving them in purified water. At this time, after throwing away non-solved ones, loess solution is kept in the dark place until sediment is observed. And the sediment is taken as a viscous materials and then mixed with the sodium chloride solution. After the mixture is agitating for 3–4 hours, the agitated mixture is added to NaOH by pH 7.0. When the agglutination is observed in the mixture, the mixture is purified to obtain the loess's extract.

If the loess's extract is mixed with the sodium chloride solution and the marine plant's extract including various ingredients extracted from the brown seaweed and the sea tangle, the viscous material of the loess's extract obtained by the ion substitution is electrically combined with the ingredients of the marine plant's extract which are in ion state, in sodium chloride solution, and consequently, the viscous material-combined body cosmetic composition are obtained.

Fourthly, it is described on the shell's extract and its extracting method.

Shells contain following ingredients shown in table 2.

| Main ingredients | CaCO$_3$ | N | P$_2$O$_5$ | K$_2$O | MgO |
|---|---|---|---|---|---|
| Content (%) | 8.6 | 0.3 | 0.3 | 0.2 | 0.7 |
| Rare ingredients | Mn | B | Zn | Fe | Cu |
| Content (ppm) | 300 | 224 | 90 | 343 | 16 |

[Table 2] Analysis table of ingredients of shells

To extract shell's extract, at first, any shells selected from oyster, clam, mussel and bivalve are pulverized finely and then mixed with water at the ratio of 1:1. At last, shell's extract is extracted by means of filtering heated mixture after the mixture is heated for about 30 minutes. Because the shell's extract includes various ingredients such as CaCO$_3$, K$_2$O, P$_2$O$_5$, N, Mg, Mn, Fe, Zn, B and so on, the shell's extract aids the sodium chloride solution, the marine plant's extract and the loess's extract to act on enhancing skin elasticity and losing a weight.

Hereinafter, examples of the present invention will be described. However, the present invention is not limited by examples.

EXAMPLE 1

1. Purification of sodium chloride solution(2.0–2.2 weight %)

i) inflow of sea water

Draw the sea water in a tank on the ground, and fit the concentration thereof to be 2.0–2.2% by measuring concentration with use of a salinity concentration measurer.

ii) purification of sea water

Preferably, a purifier, as described below, is adapted for obtaining pure sodium chloride solution by eliminating impurities in the sea water, as shown in FIG. 1 and FIG. 2.

The purifier is composed of a reservoir 1 for storing sea water to be used, turning circular filtering units 3 connected to the reservoir 1 through pipes 2, a final reservoir 4 for separating the sea water, supplied to the turning circular filtering units 3, from impurities and then storing it, a pump 5 for pumping the solution from the final reservoir 5, and a digesting filter 6 for finally filtering the solution which comes up by pumping force of the pump 5. In addition, the pipes 2, connecting the turning circular filtering units 3, are provided with a blow motor 7 for supplying air so to prevent the sea water from being contaminated by bacteria. In special, filter papers 8 in the turning circular filtering unit 3 are provided at rotating axis 9 with being constantly spaced apart for filtering impurities from the sea water.

According to the above processes, the pure sodium chloride solution is collected in the digesting filter 6 at the end via a series of the processes. The pure sodium chloride solution collected in the digesting filter 6 can be used for producing the body cosmetic composition.

2. Several ingredient extraction of the brown seaweed and the sea tangle

I) raw materials use 1 kg of crude materials of the brown seaweed and the sea tangle.

ii) deodorization remove odors by turning the raw materials with use of a concussing device at 500–1,000 RPM and rinsing during 60 minutes with streaming the aliquot water for taking off inherent odors of the brown seaweed and the sea tangle.

iii) destruction of leaf tissue break down about 50% of the leaf tissue cells through generation of the freezing point by executing process three times repeatedly in which the deodorized materials are frozen in a freezer at −5° C. during 48 hours and continuously thawed in a thawing device at 3° C. during 6 hours, so to assist several ingredients to be extracted.

iv) adding sodium chloride solution and pulverizing a mixture of the leaf tissue and the sodium chloride solution add 800 cc of the sodium chloride solution(2.0–2.2 weight %) therein, pulverize them with use of the pulverizer (Polytron pt2000) at 6000 RPM and pulverize about 90% of the leaf tissue, so to extract the several ingredients.

v) filtration extract needed solution by separating and filtering the pulverized material.

vi) pH adjustment of the extract by treating organic acid treat the filtrated extract with organic acids such as tartaric acids, citric acids, etc to adjust pH which is suitable for applying to the skin.

3. Extraction of the loess's extract including silica, aluminum, magnesium, and various minerals Pulverize the loess finely, sift two or three times with a sieve for selecting minute ones like sand, solve 100 g of them in 500 ml of the purified water, throw away the non-solved ones and select the solved ones, and then dry in the shade them during about 1 hour. Then, eliminate the purified water, take the sunk portion in bottom, mix them with the sodium chloride solution(1,000 ml), agitate them during 3–4 hours, dry them in the shade about one day, then eliminate the sunk portion in the bottom, add NaOH solution to a mixture processed by the foregoing steps until pH of the mixture is about 7.0 and sudden agglutination is generated, and purify them so to obtain viscous materials in ion state.

4. Extraction of the shell's extract including various ingredients

Oyster shells, clam shells, mussel shells or bivalve shells are pulverized finely and then mixed with water at the ratio of 1:1. The mixture is heated for about 30 minutes and then shell's extract is extracted by means of filtering heated mixture.

5. Body cosmetic water

The body cosmetic water is produced by uniformly mixing and agitating all of ingredients of the Table 3 below prepared according to aforementioned extraction method.

[TABLE 3]

| Ingredients | Body cosmetic water | Comparative Example 1 | Comparative example 2 | Comparative example 3 | comparative example 4 |
|---|---|---|---|---|---|
| Sodium chloride solution | By weight (to 100) | 100 | 100 | 100 | — |
| Marine plant's extract | 20 | 20 | — | 20 | 20 |
| Loess's extract | 10 | 10 | 10 | — | 10 |
| Shell's extract | 5 | — | 5 | 5 | 5 |
| Paraoxybenzoic propyl | 0.1 | 0.1 | 0.1 | 0.1 | 0.1 |
| Colorant | Suitable amount | Suitable amount | Suitable amount | Suitable amount | suitable amount |
| Compounded perfume | 0.1 | 0.1 | 0.1 | 0.1 | 0.1 |

EXAMPLE 2

The other body cosmetic water is also produced by uniformly mixing and agitating all of ingredients of Table 4 prepared according to the same method of example 1 except for containing ratio of each ingredient.

[TABLE 4]

| Ingredients | Body cosmetic water | Comparative Example 1 | Comparative example 2 | Comparative example 3 | Comparative example 4 |
|---|---|---|---|---|---|
| Sodium chloride solution | by weight (to 100) | 100 | 100 | 100 | — |
| Marine plant's extract | 30 | 30 | — | 30 | 30 |
| Loess's extract | 20 | 20 | 20 | — | 20 |
| Shell's extract | 7 | — | 7 | 7 | 7 |
| Paraoxybenzoic propyl | 0.1 | 0.1 | 0.1 | 0.1 | 0.1 |
| Colorant | Suitable amount | Suitable Amount | Suitable amount | Suitable amount | Suitable amount |
| Compounded perfume | 0.1 | 0.1 | 0.1 | 0.1 | 0.1 |

Example 3

Another body cosmetic water is also produced by uniformly mixing and agitating all of ingredients of Table 5 prepared according to the same method of example 1 except for containing ratio of each ingredient

[TABLE 5]

| Ingredients | Body cosmetic water | Comparative Example 1 | Comparative example 2 | Comparative example 3 | comparative example 4 |
|---|---|---|---|---|---|
| Sodium chloride solution | by weight (to 100) | 100 | 100 | 100 | — |
| Marine plant's extract | 40 | 40 | — | 40 | 40 |
| Loess's extract | 30 | 30 | 30 | — | 30 |
| Shell's extract | 10 | — | 10 | 10 | 10 |
| Paraoxybenzoic propyl | 0.1 | 0.1 | 0.1 | 0.1 | 0.1 |
| Colorant | Suitable amount | Suitable Amount | Suitable amount | Suitable amount | suitable amount |
| Compounded perfume | 0.1 | 0.1 | 0.1 | 0.1 | 0.1 |

Comparative test of application sensitivity, durability and safety

Herein, application sensitivity means to degree of recovering skin elasticity and losing a weight by decreasing lipid, durability means to degree of keeping the application sensitivity, and safety means to degree of appearing side effect.

The products and the comparative examples 1–4 produced according to examples 1, 2, and 3 are tested by 20 persons for 3 months. Each of them gave points from 1 to 5 per the test item, and the points are averaged. Point 5 means very excellent, point 4 means excellent, point 3 means normal, point 2 means poor, and point 1 means very poor. The results of the test to examples 1,2, and 3 will be described respectively table 6,7 and 8.

[TABLE 6]

| test item | Body cosmetic Water | comparative example 1 | Comparative example 2 | Comparative example 3 | comparative example 4 |
|---|---|---|---|---|---|
| Application | 4.6 | 4.1 | 3.8 | 3.9 | 3.7 |
| Durability | 4.6 | 4.0 | 3.8 | 3.8 | 3.7 |
| Safety | 4.5 | 4.3 | 4.2 | 4.0 | 4.0 |

[TABLE 7]

| test item | Body Cosmetic water | Comparative Example 1 | comparative example 2 | Comparative example 3 | comparative example 4 |
|---|---|---|---|---|---|
| Application | 4.8 | 4.5 | 4.1 | 4.2 | 4.0 |
| Durability | 4.7 | 4.2 | 4.0 | 4.1 | 4.0 |
| Safety | 4.6 | 4.6 | 4.5 | 4.0 | 4.0 |

[TABLE 8]

| Test item | Body cosmetic water | comparative example 1 | comparative example 2 | Comparative example 3 | Comparative example 4 |
|---|---|---|---|---|---|
| Application | 4.6 | 4.1 | 3.9 | 3.9 | 3.8 |
| Durability | 4.6 | 4.0 | 3.9 | 4.0 | 3.9 |
| Safety | 4.5 | 4.3 | 4.2 | 4.0 | 4.0 |

As considered through the above results, the body cosmetic waters according to examples 1, 2 and 3 are respectively compared with comparative example 1, it is known that the shell's extract helps the sodium chloride solution, the marine plant's extract and the loess's extract to act to their effects and may increase durability of the body cosmetic water.

In particular, the body cosmetic water which comprises 30 weight part of marine plant's extract, 20 weight part of loess's extract, and 7 weight part of shell's extract per 100 weight part of sodium chloride solution has excellent application sensitivity, durability and safety.

As described above, the body cosmetic composition of the present invention provides elasticity in skin, particularly excessively sagged muscles and has an effect of losing a weight. In addition, the cosmetic composition contributes to prevent the skin from aging by providing the inorganic substance, the mineral and the like for skin cells through the capillary vessel connected to the skin, and further give effects to maintain physical fitness.

What is claimed is:

1. A method for producing a body cosmetic composition, wherein the method comprises steps of:
   1) purifying a sodium chloride solution from sea water and obtaining the sodium chloride solution which has a concentration of about 2.0–2.2 weight %;
   2) obtaining a marine plant extract from marine plant material selected from the group consisting of brown seaweeds, sea tangles and combinations thereof by steps of:
      a) treating the marine plant material with 1–5 freeze-thaw cycles, wherein the freeze cycles are carried out at temperature from −7° C. to −3° C. for 48 hours and the thaw cycles are carried out at temperature from 1° C. to 5° C. for 6 hours;
      b) adding the sodium chloride solution which has a concentration of about 2.0–2.2 weight % to the treated marine plant material to form a mixture;
      c) pulverizing the mixture until the treated marine plant material is broken down more than 90%;
      d) filtrating the pulverized mixture; and
      e) treating the filtrated mixture with organic acid to adjust pH, which is suitable for applying to the skin;
   3) obtaining a loess extract from loess materials selected from the group consisting of kaolinite, montmorillonite and combinations thereof by means of using the sodium chloride solution;
   4) obtaining a shell extract from shells selected from the group consisting of oyster shells, clam shells, mussel shells, bivalve shells and combinations thereof; and
   5) mixing the sodium chloride solution, the marine plant extract, the loess extract and the shell extract with at least one additive uniformly to form a body cosmetic composition.

2. The method for producing a body cosmetic composition of the claim 1, wherein the step of obtaining the loess extract further comprises the steps of:
   a) separating minute loess by means of pulverizing loess materials and then screening the pulverized loess;
   b) obtaining a loess solution by means of dissolving the minute loess in a purified water;
   c) extracting viscous materials including silica, Al, Mg and various minerals by means of taking a sunk portion of the loess solution which is kept in the dark place;

d) mixing the viscous materials with the sodium chloride solution which has a concentration of about 2.0–2.2 weight % to form a viscous material solution;

e) filtrating the viscous material solution after agitating for 3–4 hours; and f) obtaining the loess extract by means of adding NaOH to the filtrated solution until sudden agglutination is observed, and then purifying the solution.

3. The method for producing a body cosmetic composition of the claim 1, wherein the step of obtaining the shell extract further comprises the steps of:

a) pulverizing the shells;

b) mixing the pulverized shells with water at the ratio 1:1;

c) heating the mixture for 30 minutes; and d) filtrating the heated mixture to obtain the shell extract.

4. The method for producing a body cosmetic composition of claim 1 wherein the additive is selected from the group consisting of fragrance, preservative, colorant and useful material for skin health.

* * * * *

UNITED STATES PATENT AND TRADEMARK OFFICE
CERTIFICATE OF CORRECTION

| | | |
|---|---|---|
| PATENT NO. | : 6,365,162 B1 | Page 1 of 1 |
| DATED | : March 12, 2002 | |
| INVENTOR(S) | : Yves DeFlandre, Marc Hoffman and Gray Cyr | |

It is certified that error appears in the above-identified patent and that said Letters Patent is hereby corrected as shown below:

Column 2,
Line 18, please replace "modem" with -- modern --.

Column 7,
Line 62, after the word "as" please insert -- a --.

Signed and Sealed this

Eighteenth Day of June, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.    : 6,365,162 B1
DATED         : April 2, 2002
INVENTOR(S)   : Ho Chin Sim It is certified that error appears in the above-identified patent and that said Letters Patent is hereby corrected as shown below:

This Certificate supersedes Certificate of Correction issued June 18, 2002, the number was erroneously mentioned and should be vacated since no Certificate of Correction was granted.

Signed and Sealed this

Fourth Day of February, 2003

JAMES E. ROGAN
*Director of the United States Patent and Trademark Office*